United States Patent
Bettin et al.

(10) Patent No.: US 7,896,019 B2
(45) Date of Patent: Mar. 1, 2011

(54) ACTIVE CONTROLLED ENERGY ABSORBER USING RESPONSIVE FLUIDS

(75) Inventors: Giorgia Bettin, Cambridge, MA (US); Suraj S. Deshmukh, Cambridge, MA (US); Gareth H. McKinley, Acton, MA (US)

(73) Assignee: Massachusetts Institute for Technology, Cambridge, MA (US)

( * ) Notice: Subject to any disclaimer, the term of this patent is extended or adjusted under 35 U.S.C. 154(b) by 1220 days.

(21) Appl. No.: 11/270,971

(22) Filed: Nov. 12, 2005

(65) Prior Publication Data

US 2007/0107778 A1 May 17, 2007

(51) Int. Cl.
*F17D 1/16* (2006.01)
*F16F 9/53* (2006.01)

(52) U.S. Cl. .................. 137/13; 188/267.1; 188/322.5
(58) Field of Classification Search ............. 137/13; 188/266, 267.1, 322.5
See application file for complete search history.

(56) References Cited

U.S. PATENT DOCUMENTS

| | | | | |
|---|---|---|---|---|
| 2,756,016 A | * | 7/1956 | Giles | 267/140.13 |
| 4,381,491 A | * | 4/1983 | Vogelgesang | 335/257 |
| 6,701,529 B1 | * | 3/2004 | Rhoades et al. | 2/2.5 |

FOREIGN PATENT DOCUMENTS

DE 4213513 A1 * 10/1993

* cited by examiner

*Primary Examiner* — John Rivell
(74) *Attorney, Agent, or Firm* — Charles G. Call

(57) ABSTRACT

An impact absorber employs dilatant (shear responsive) fluid that is subjected to a controlled, low amplitude, high frequency oscillatory stress which controls the stiffness of the fluid. Piezoelectric transducers, voice coils, and other forms of transducers may be used to apply controlled vibratory stress to the fluid. The energy absorber may be used in protective body armor, medical devices such as splints and casts, vehicle safety absorbers and many other products which benefit from ability to control the stiffness of the energy absorber.

14 Claims, 8 Drawing Sheets

ACTIVE CONTROLLED ENERGY ABSORBER USING RESPONSIVE FLUIDS

FEDERALLY SPONSORED RESEARCH

This invention was made with government support under Grant No. DAAD19-02-D-0002, awarded by the Army. The government has certain rights in the invention.

FIELD OF THE INVENTION

This invention relates to energy absorbing materials and structures.

BACKGROUND OF THE INVENTION

Energy absorption materials are commonly encountered in everyday life: from bubble wrapping and Styrofoam, classically used for packaging protection; to car bumpers, fenders and headrest foam used in vehicle industry; to shoe soles, human protection gear and sports equipment. The use and need for energy absorption materials are countless as are the different materials, and at times, mechanisms used for this purpose. Generally, energy-absorbing pads are made from polymeric foams, or sometimes, polymeric materials (rubber). At times they also include mechanisms like fluid pockets, piston-like fixtures, springs, and any combinations of the above.

The reason for the many varieties is that each pad or material is tailored for a specific type of impact. The difficulty of choosing the right material arises from the fact that compliant materials, which are more comfortable to wear, are very good at absorbing small impact energies, but "bottom out" or saturate and became no longer useful if input energies are large. On the other hand stiffer materials are able to absorb a large amount of energy but are typically uncomfortable as they do not readily conform to shape, and therefore do not adhere to the surface. This can be a big problem for human protective gear like orthopedic supports, bulletproof vests, helmets, etc. This is a well-known problem commonly referred to as the "conflict of stiffness".

Energy absorption materials can be classified as "passive" and "active" materials. Passive materials have specific material characteristics that cannot be varied; for example foams or polymeric materials. These are the most common class of energy absorbing materials and are also the simplest. Active materials on the other hand can be controlled and their material properties changed in order to tailor their energy absorbing characteristics to different impact loading. A few examples of these materials are described in the U.S. patents discussed below. These material can be optimized, a priori, to work over a range of impact energies, and are normally characterized by only two states, an "off state," compliant and comfortable; and "on state," stiff and energy absorbent. The change in the amount of energy absorption or the "gain" is chosen a priori. The mechanism of activation is normally the impact itself, rather then external activation and requires specific and ideal conditions such as large deformations. These materials are efficient, but they rely on passive activation and cannot be "actively tuned" through external user control to best match a given operational setting.

In the myriad applications of energy management there is the need for a controllable, adaptive and active energy absorbing material. For example, such a material with these characteristics could be used in shoes, for which the stiffness of the sole could be actively adapted to the user's weight and the type of terrain encountered. Another possible application could be in sports equipment; for example, hollow ski bodies filled with this material would allow the skier to actively control the ski's flexibility. Another class of potential applications for these materials is in medical devices wherein, if the material could be tuned to be extremely stiff, it could be used to create adjustable splints or braces. Imagine putting on a soft sleeve to the patient's arm or leg until it is in the right position and then turning the material on and it becomes a rigid cast. Another possible application could be in the field of firearms; for example, these active tunable materials could be used to absorb the shock from a gun's recoil.

Numerous earlier patents have dealt with the development of materials for "passive" energy management; for example, absorbing, dissipating and/or shunting energy. Fluids and fluid flow have been an integral part of many of these patents because of their energy dissipation and load shunting characteristics. Some examples are U.S. Pat. No. 5,564,535 issued to J. N. Kanianthra, U.S. Pat. No. 3,672,657 issued to B. O. Young et al., and U.S. Pat. No. 5,915,819 issued to E. Gooding that describe structures comprising of a plurality of fluid-filled cells or reservoirs, wherein energy dissipation is achieved through restriction of fluid-flow through orifices or in-between cells and reservoirs. Fluids have also been used to form the underlying matrix of the structure itself so as to provide a damping or a load shunting effect. For example, World Patent No. 09949236 describes an energy absorbing material wherein elastomeric capsules are dispersed in a matrix liquid.

However, none of these structures provide energy management over a large dynamic operating range. As the magnitude of applied forces increases, an increasing device stiffness or thickness is required to prevent the material from saturating or "bottoming out". These structures thus necessitate a trade-off between user comfort and device rigidity, and are prone to changes in ideal external conditions. On the other hand, devices employing a shear-thickening (dilatant) fluid can be designed to be comfortable and compliant under lower applied stresses and naturally increase in rigidity as the applied loads or forces increase. As described below, the present invention employs a shear-thickening fluid which has a self-adjusting viscosity and hence its utility extends to a large dynamic operating range.

U.S. Pat. No. 5,545,128 issued to W. C. Hayes et al. and U.S. Pat. No. 6,701,529 issued to L. J. Rhoades et al. also employ shear-thickening (dilatant) fluids for energy dissipation by incorporating them in bladders, envelopes or cells. These structures are able to provide a large operating range; however, they suffer from a lack of controllability tunability and adaptability. They are "passive," that is are dependent upon and responsive to ideal and specific external loads only. Thus, under a given set of external conditions and forces, the energy dissipation in these devices is passively fixed and independent of the user demand or specified requirements. Further these materials cannot be used in medical devices such as splints and braces since there is no mechanism to activate them into a rigid cast.

U.S. Pat. No. 4,759,428 issued to K. Seshimo, U.S. Pat. No. 4,852,533 issued to F. Doncker et al., and U.S. Pat. No. 5,645,138 issued to H. Takima et al. describe systems in which dilatant materials are used to suppress vibrations (and respond differently to different frequency vibrations), but provide no mechanism for controlling stiffness in order to manage anticipated impacts. In these prior systems, energy absorption is optimum only at a single deformation rate rather than for the different rates that practical devices will encounter during use.

SUMMARY OF THE INVENTION

The present invention takes the form of methods and apparatus for controlling the rheological properties of a dilatant material by imposing a controlled, oscillatory deformation from an external source to subject the material to a controlled deformation rate which varies the viscosity of the material. The stiffness of the material may be controlled by varying the magnitude or the frequency (or both) of the applied oscillatory deformation stress. The applied stress may be varied within a range in which the viscosity of the dilatant material varies as said controlled deformation varies.

Preferred embodiments of the invention provide an active energy management structure which employs a dilatant (stress responsive) material to absorb or redistribute impact energy, and includes one or more transducers for applying a controlled vibratory stress or strain to the dilatant material that increases its viscosity as the applied rate of deformation increases. A sensor coupled to the transducer(s) that is responsive to the actual or anticipated magnitude of an impact may be used to automatically vary the controlled vibratory stress or strain to increase said viscosity as the magnitude increases.

The transducers and the shear responsive fluid reservoir may take the form of a shaped or flexible absorber that can be worn on the body as protective, impact absorbing body armor. A controlled impact absorber implementing the invention may be used to protect vehicle occupants against crash injuries, as an adjustable recoil pad used with firearms, as a cushioned support of controllable stiffness used in athletic shoes, and in many other applications which benefit from the invention's ability to tune and control the stiffness of an impact absorber under different circumstances.

These and other features, advantages and applications of the invention may be more clearly understood by considering the following detailed description of specific embodiments of the invention. In the course of this description, frequent reference will be made to the attached drawings.

DETAILED DESCRIPTION

Figure 1:
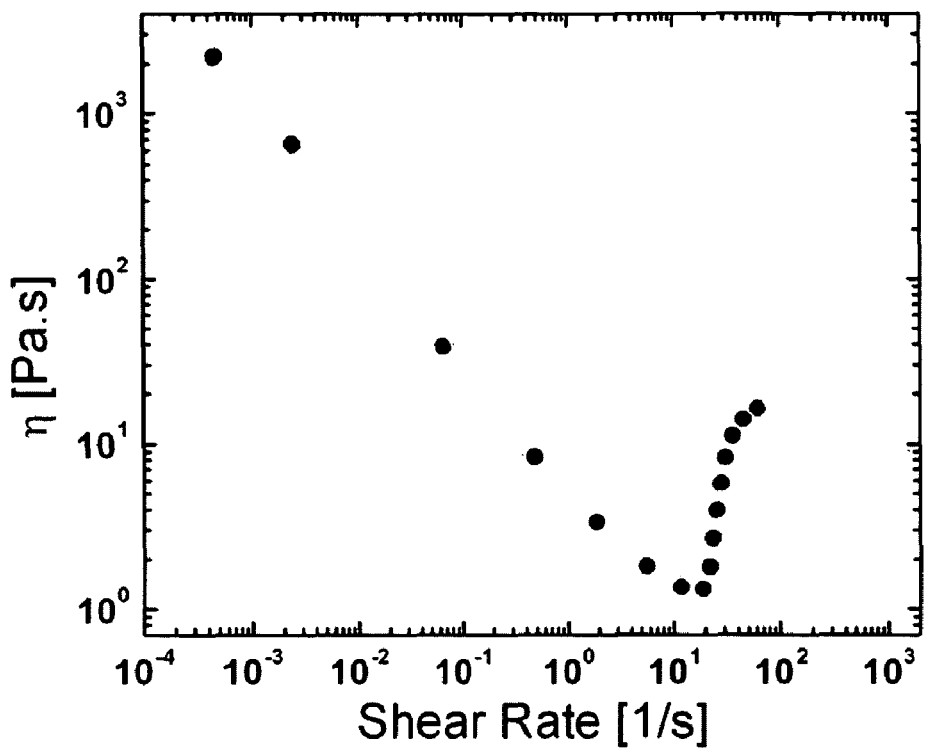
FIG. 1 is a plot showing the viscosity of a dilatant material, such as a highly concentrated suspension, as a function of shear rates.

The description that follows defines a number of terms and explains certain concepts by way of introduction:

Viscosity: Viscosity is a measure of a material's resistance to flow. It is calculated as the ratio of the shear-stress to the shear-rate.

Stress: Stress is a distribution of forces over an infinitesimal area.

Strain: Strain is a measure of a body's change in shape. The change in strain with time is the strain rate.

The rate of deformation or the rate at which adjacent layers of fluid move is the shear rate.

Hooke's law: Hooke's law defines the mechanical behavior of an ideal solid, relating the applied strain ($\epsilon$ or $\gamma$) to the resultant stress ($\sigma$ or $\tau$) through a factor called the modulus (E or G). Thus, $\sigma = E\epsilon$ (tension, bending) or $\tau = G\gamma$ (shear). The modulus is a measure of the material's stiffness (i.e., its ability to resist deformation). The linear region in which the modulus does not change when the strain is changed is called the Hookean region.

Newton's Law: Newton developed a relationship similar to Hooke's law for ideal viscous fluids, relating the stress ($\tau$) linearly to the shear rate ($d\gamma/dt$). Thus, $\tau = \mu\, d\gamma/dt$, where $\mu$ is the coefficient of viscosity. A fluid is Newtonian if, when sheared, its viscosity does not depend on shear rate.

Newtonian Versus Non-Newtonian Flow: Water and mineral oil are Newtonian, but not many other materials behave this way. Most fluids are non-Newtonian, their viscosity changing with changes in shear rate. This means the expression $\tau = \mu\, d\gamma/dt$, where $\mu$ is constant, is only valid at a particular shear rate. Changing the shear rate changes the viscosity. Various types of non-Newtonian behavior are known, differing by how the viscosity changes with shear rate, and whether or not the flow pattern is time-dependent. The time-independent types are called Bingham, pseudoplastic (shear-thinning), and dilatant (shear-thickening); the time-dependent types are called thixotropic and rheopectic.

For Bingham fluids, a critical yield stress ($\tau_c$) must be exceeded before flow begins. Until then, the material behaves as a Hookean solid; beyond $\tau_c$, it behaves as a Newtonian fluid. No-Drip paints and ketchup are Bingham fluids.

In contrast with Bingham fluids, most fluids show a curvature in their stress versus strain rate curves after exceeding the critical stress, and the apparent viscosity increases or decreases with the rate of deformation. This is exhibited, for example, by toothpaste, lipstick, and oil drilling muds.

For many materials, flow begins as soon as a deformation rate is applied. If the fluid's viscosity decreases with increasing shear rate, the phenomenon is described as being shear-thinning (or pseudoplastic). Molten polymers, polymer solutions, bread dough, and a variety of suspensions, emulsions and other structured fluids used as pharmaceuticals and cosmetics exhibit pseudoplastic flow.

Moist sand, PVC plastisols, aqueous suspensions of penicillin powder, and other densely packed dispersions increase in viscosity when they are sheared at an increasing rate. After the altered structure stabilizes, at a constant deformation rate the viscosity becomes constant. This shear behavior is called dilatancy and materials that exhibit that behavior are called dilatant or shear-thickening materials.

Preferred embodiments of the present invention employ an adaptive active mechanism for energy absorption that uses dilatant fluids which can be rapidly and reversibly actuated by imposing small amplitude high frequency oscillations. The dilatant fluid is a highly concentrated suspension disperse and stabilized in a carrier fluid that behaves like a low conventional viscosity fluid when low shear rates are applied but increases its viscosity and ultimately solidifies at high shear rates. FIG. 1 illustrates an example of the viscosity of a dilatant fluid as a function of shear rates. These fluids have been used in the past for energy absorption because of their thickening characteristics, as noted above, but they have always been used passively without any control, relying on impact for activation.

There are two ways to achieve shear-induced thickening of these dilatant fluids: the first which has been exploited in the past is achieved by applying a large deformation or strain at a high enough rate. See, for example: S. N. Robinovitch, W. C. Haynes, T. A. McMahon, *Energy-shunting hip padding system Attenuates femoral impact forces in a simulated fall*. Journal of Biomechanical Engineering, 1995. 117: p. 409-413; and Young S. Lee, Erik D. Wetzel, Norman J. Wagner, *The ballistic impact characteristic of Kevlar woven fabrics impregnated with a colloidal shear thickening fluid*. J. Mat. Sci., 2003. 38(13): p. 2825-2833.

Figure 2:
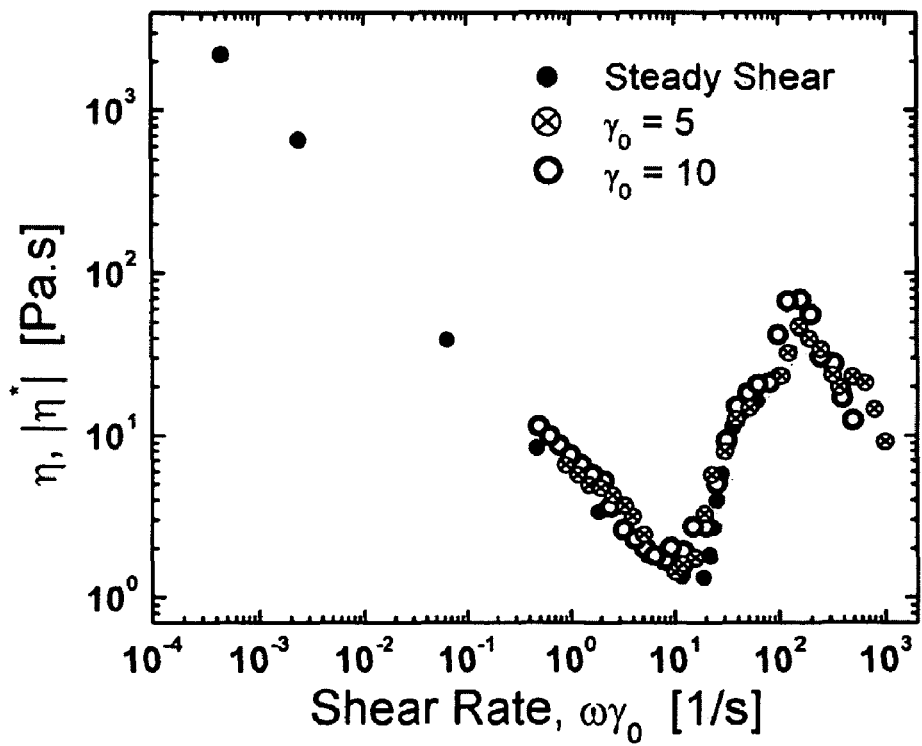
FIG. 2 is a plot showing the viscosity of a dilatant material, such as a highly concentrated suspension, as a function of shear rates, superimposed on the magnitude of complex viscosity obtained for various magnitudes and frequencies of oscillatory shearing motion.

The second way, which is implemented by the preferred embodiments of the present invention, achieves shear-induced thickening by inducing a localized rapidly varying shear field. One way to achieve this is to apply a small amplitude high frequency oscillation to the dilatant fluid. When oscillating, the effective strain rate applied on the fluid is defined as $\dot{\gamma}=\gamma_0\omega$, where $\gamma_0$ is the amplitude of the shear strain and $\omega$ is the frequency at which it is applied. Effectively, oscillating at a frequency $\omega$ at a shear strain $\gamma_0$ is equivalent to a large strain deformation at a shear rate $\dot{\gamma}\gamma_0\omega$ as illustrated in FIG. 2. This effect has been reported in the literature. This effect has been reported in the literature. See, for example; Raghavan, S. R. and S. A. Khan, *Shear-thickening response of fumed silica suspensions under steady and oscillatory shear*. Journal of Colloid and Interface Science, 1997. 185(1): p. 57-67; and N. J. Wagner, Y. S. Lee, *Dynamic properties of shear thickening colloidal suspensions*. Rheologica Acta, 2003. 42: p. 199-20.

Figure 3:
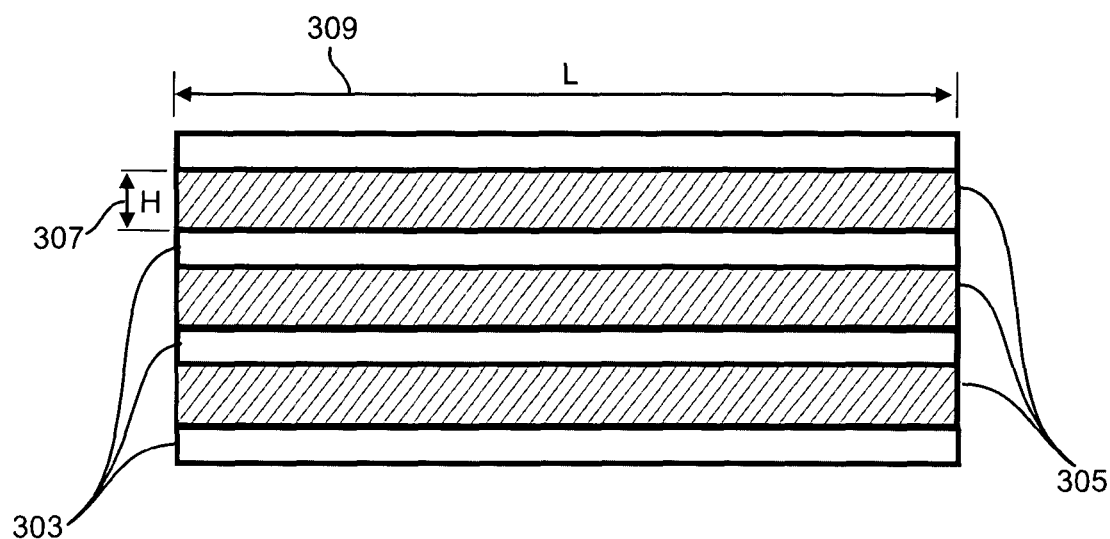
FIG. 3 is a cross-sectional view showing the geometry of an energy absorption mechanism in which a dilatant fluid is sandwiched in between oscillating plates.
Figure 4:
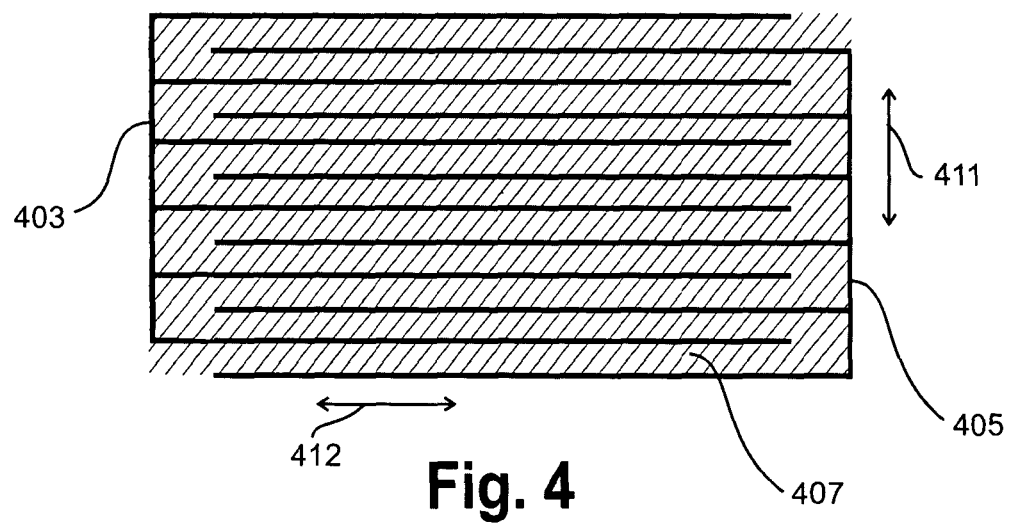
FIG. 4 is a cross-sectional view showing a second dilatant fluid based sandwich structure.

The construction of the material/mechanism might consist of, but is not limited to, a layer of dilatant fluid sandwiched between two oscillating plates and it could be expanded to multiple layers. As seen in FIG. 3, piezoelectric plates 303 sandwich layers of dilatant fluid seen at 305. As seen in FIG. 4, two plate structures seen at 403 and 405, each consisting of several parallel plates mechanically connected together, are interleaved and separated by a dilatant fluid 407. In both FIGS. 3 and 4, the plates may oscillate in two alternative modes, one of which is normal to the surface of the plates as indicated at 411 and the other mode of oscillation being parallel to the plane of the plates as indicated at 412. The viscosity of the fluid sandwiched in between the layers is controlled by the amplitude and frequency of the plate oscillation according to FIG. 2.

Figure 5:
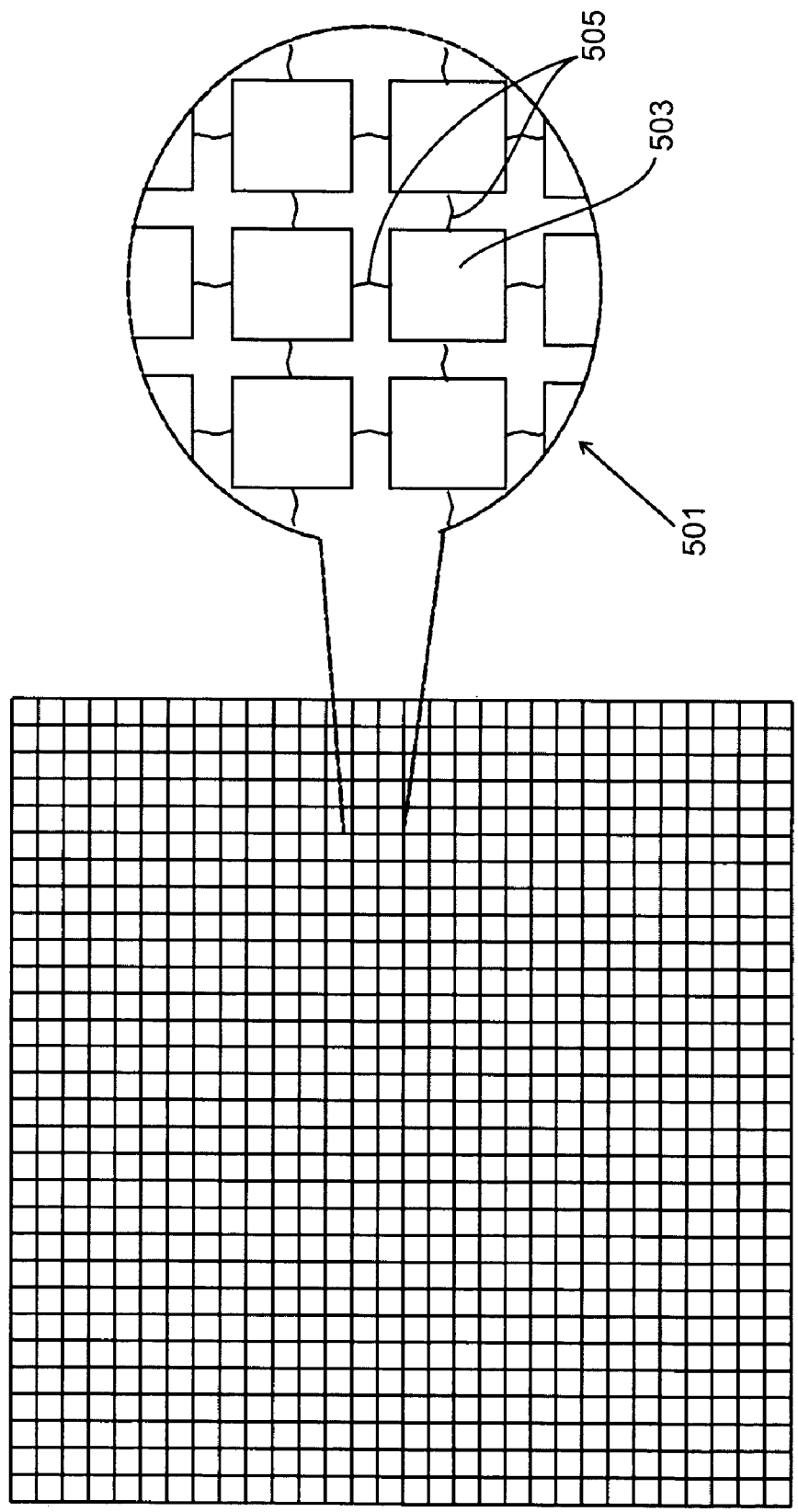
FIG. 5 illustrates a geometry for an absorber formed as a flexible oscillating sheet consisting of an array of individual piezoelectric transducers.

The plates do not necessarily need to be rigid in their entirety, but can be an array of small oscillators that can bend relative to each other, as in a flexible frame illustrated in FIG. 5 which consists of rectangular array of individual oscillating plates seen enlarged at 501. Each plate 501 consists of a piezoelectric device which is energized from a variable frequency, variable amplitude voltage source (not shown) via conductors 505 which interconnect all of the plates in the array with the voltage source.

A very important consideration is the magnitude of the strain obtainable by the oscillating plates. When a fluid is sandwiched or squeezed in between two plates, the magnitude of the vertical strain to the shear strain felt by the fluid is a function of the aspect ratio between the height and length, as given by the following relation:

$$\dot{\gamma}_{local} \propto \left(\frac{L}{H}\right)^2 \dot{\varepsilon}$$

where $\dot{\gamma}_{local}$ is the local shear strain rate experienced by the fluid, H is the gap height (seen at 307 in FIG. 3), L is the plate length (seen at 309 in FIG. 3) and $\dot{\varepsilon}$ is the vertical rate of oscillation of the plates, equivalent to $\dot{\varepsilon}=\epsilon_0\omega$. This is a well known result and is usually referred to as a squeeze flow or "lubrication effect." The factor $(L/H)^2$ can be considered to be a magnification factor. The magnitude of oscillation supplied by the plates can be limited by choosing a geometry that has a large magnification ratio.

As an example only, consider an oscillating plate obtained by placing a number of small piezo transducers in an array of the type illustrated in FIG. 5. The amplitude of oscillations, (typically being on the order of microns) can be amplified by carefully choosing the geometry and utilizing squeeze flow. By applying voltages to the piezoelectric plates between 1V-10 KV, vertically oscillating amplitudes as large as 30 microns can be obtained. With a gap of 150 microns and a lateral piezoelectric plate size of 1 cm we can achieve local strain rates that exceed $\dot{\gamma}_{local}\approx 5000$ s$^{-1}$ (which corresponds, as seen in FIG. 2, to discontinuous shear thickening and solidification of the sample.)

Commercial Applications

Using the principles of the invention, shear-thickening fluids can be actively controlled and excited instantly to a desired viscosity state. The ability to control the viscosity of shear thickening fluids by subjecting the fluids to controlled vibratory oscillations has potential applicability in a number of areas. Applications utilizing these adaptive properties will typically consist of shear-thickening fluids in the desired geometry with transducers in the form of plates, sheets or stacks and associated electronics to control the frequency and amplitude of oscillations and to provide power to the transducers. Illustrative applications of the principles of the invention are described individually below. Energy absorbing materials and structures which embody the invention may be used in applications ranging from ballistic armor, devices used in automotive industry, helmets, sporting equipment, protective clothing, biological splints and many other devices.

Figure 6:
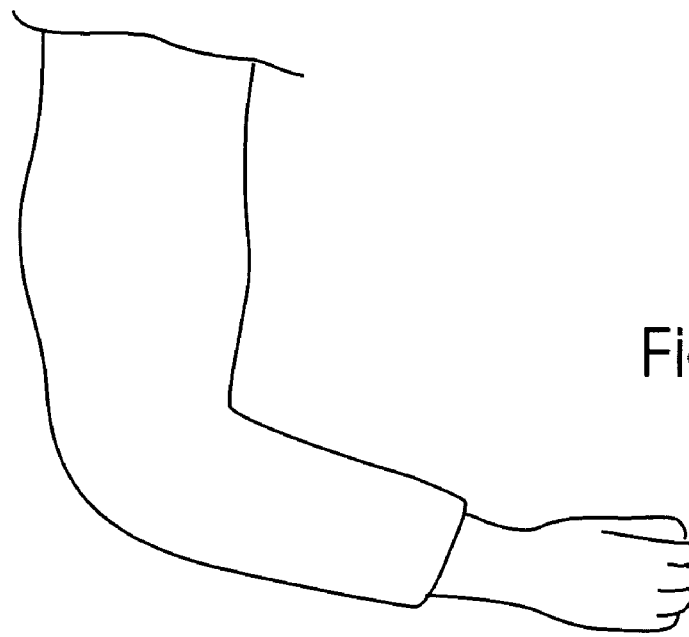
FIG. 6 illustrate protective clothing that is formed using a flexible sheet material of the type shown in FIG. 5 or 7.
Figure 7:
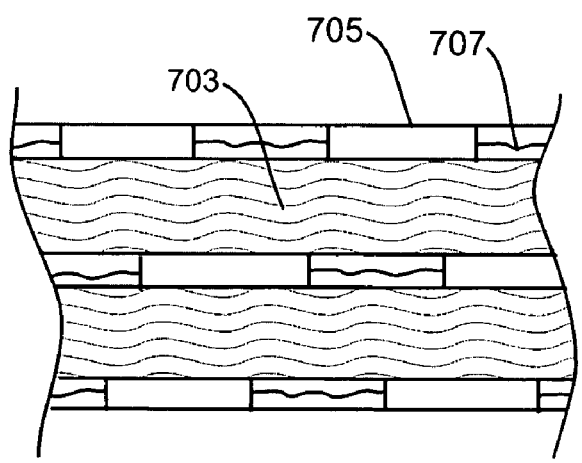
FIG. 7 is a cross-sectional view of a flexible fabric consisting of two dilatant fluid layers sandwiched between three layers containing oscillating piezoelectric plates.

Ballistic Armor applications: Impact protection and ballistic protection is the primary function of a soldier's body armor. User-controllable energy dissipation through shear-thickening fluid impregnated clothing could serve the dual purpose of providing comfort under normal use and protection from impact and blunt trauma in threat-posing conditions. The present invention could also prove useful for controllable blast protection, vibration dissipation and recoil reduction in military equipment and weaponry systems. For example, the protective clothing seen in FIG. 6 is formed from a flexible "fabric" seen in FIG. 7 consisting of two layers of dilatant fluid 703 sandwiched between three layers that contain arrays of separate oscillating piezoelectric plates 705 interconnected by conductors 707 which apply a controllable voltage to the individual plates. When the wearer is not in a threatening situation, the plates can remain de-energized, but when needed, an oscillating voltage is applied to the piezoelectric plates 705 to subject the fluid to high frequency, low amplitude oscillations, causing the fluid 703 to stiffen and thus protect the wearer from impact. The composite material consisting of the layers of dilatant fluid and energizable sources of oscillation can thus be used to provide protective armor and clothing which is relatively comfortable to wear when de-energized but which provides the needed impact protection when needed.

Protective clothing and Medical devices: The human body is susceptible to damage due to external stress, impact and shocks. Protective clothing and garments such as orthopedic supports, braces, splints, slings and wraps are commonly used for injury, fracture prevention and protection. These garments or devices usually use fluid or foam based padding materials together with a rigid load-bearing frame that surrounds the susceptible body tissues and bones for energy dissipation and load shunting. The present invention would prove useful in these and numerous other protective devices for a large range of conditions that are experienced in everyday use such as normal use to simple bruises, cuts to high-impact physical activity and accidents. Further, devices based on the technology described in the present invention have an added advantage of being user-controllable.

Figure 8:
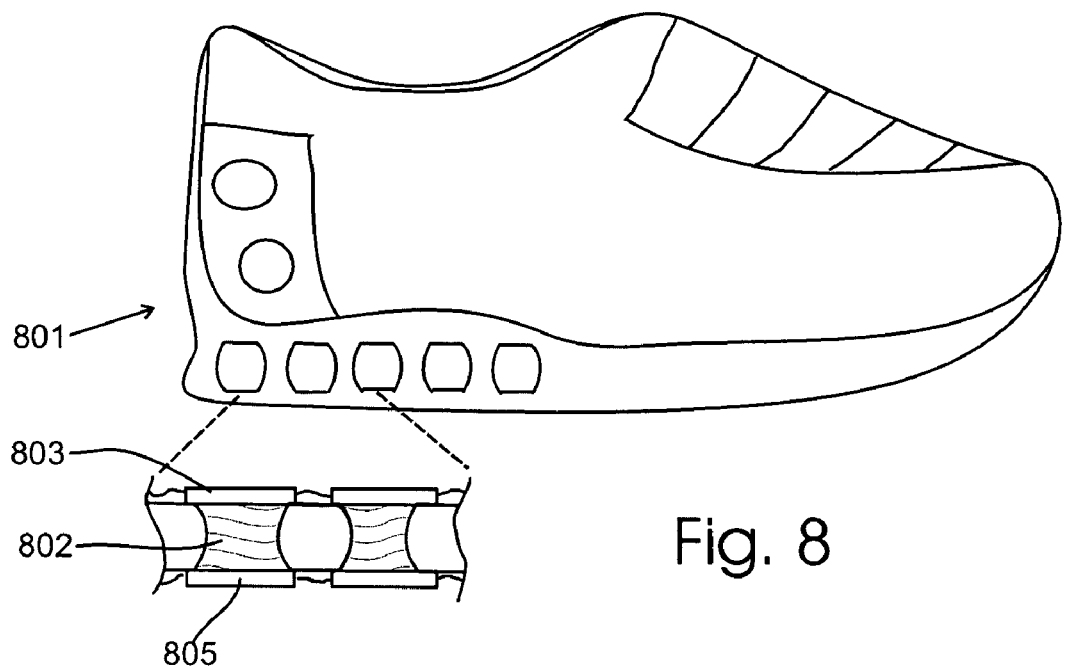
FIG. 8 illustrates a shoe equipped with a heel cushion having controllable stiffness.
Figure 9:
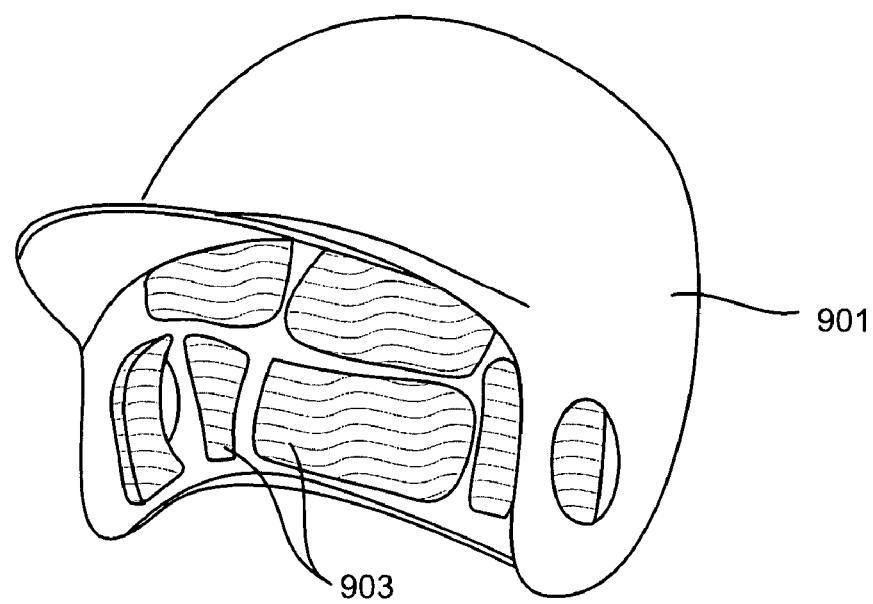
FIG. 9 shows a helmet lined with absorptive padding having controllable stiffness.

Sporting gear and equipment: Sporting gear like shoes, helmets, gloves, supports and braces is commonly used for both comfort and injury prevention. A fluid-based device is especially useful since it is conformable to the body part in contact and, in the case of a shear-thickening fluid, the energy absorption capacity of the device self-adjusts to the applied loads, stresses. These comfort, compliance and protection characteristics of the device can further be actively controlled using an imposed stress deformation field as described in the present invention. FIGS. 8 and 9 show the use of externally imposed oscillations to 'activate' shear-thickening fluid in sporting gear and equipment such as shoes and helmets. In the shoe seen in FIG. 8 at 801, an impact absorbing heel cushion is formed to hold a dilatant fluid in cavities, one of which is shown enlarged at 802. Piezoelectric plates 803 and 805 are positioned in contact with the fluid 802 which is sandwiched between the two plates. A controllable voltage source (not shown) can be used to vary the intensity of the oscillations applied to the fluid by the plates to control the stiffness of the heel cushion as desired for different conditions. For example, a softer setting may be used for walking, and a stiffer setting used for running when impact forces are higher and would cause the heel cushion to "bottom out" at the softer setting.

Figure 10:
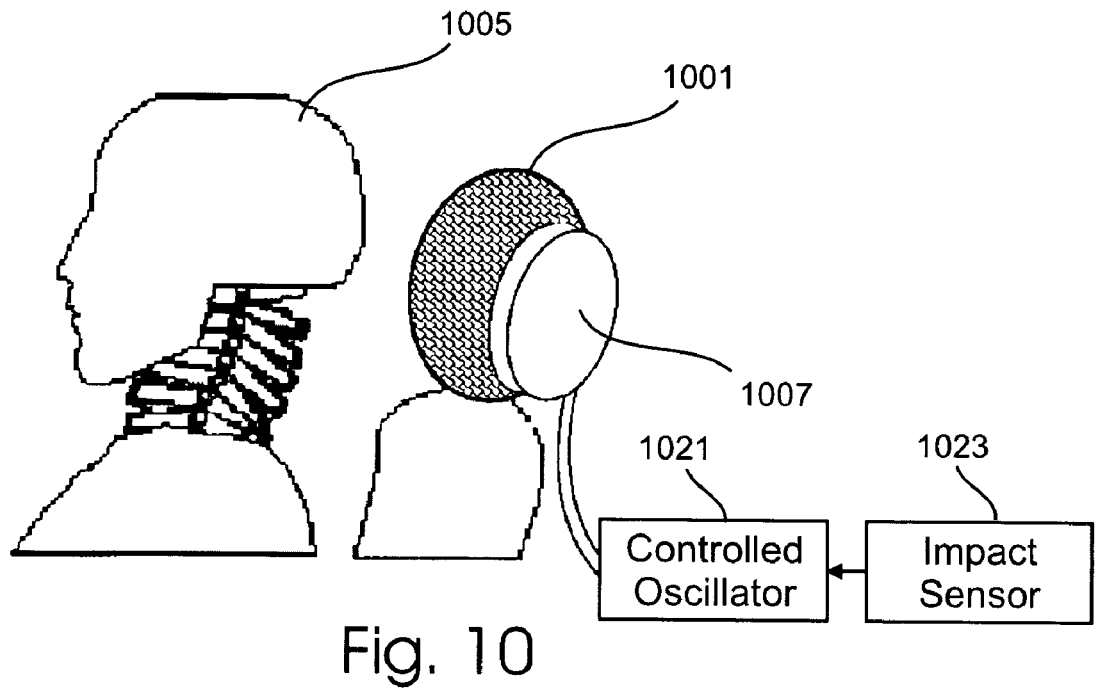
FIG. 10 shows an automotive driver or passenger headrest having controllable stiffness.

Energy management for Automobile applications: Automobiles require a wide array of energy absorbing structures, and energy management for passenger safety and comfort is an important concern. The seat backrest and headrest provide comfort to the passenger by absorbing small shock energies under normal driving conditions. The knee bolster located below the steering wheel absorbs impact from the passenger's knee during a frontal crash. The A/B/C pillar trims cushion the shock to the passenger head in a frontal or side-car impact. Also, crumple zones or deliberate weak spots in strategic locations collapse in a controlled manner during a crash to dissipate energy. The principles of the present invention may be employed to allow all these structures to be adaptive to different passenger-dependent protection requirements while also being compliant and comfortable under normal driving conditions. FIG. 10 illustrates a headrest 1001 containing a dilatant fluid used to provide soft comfortable support to the driver's head 1005 during normal driving conditions, but which can be energized by a source of high frequency oscillations from controlled oscillation source 1021 in response to an actual or anticipated impact detected by a sensor 1023. For example, the same sensors used to trigger air bags in automobiles can be used to apply oscillations to stiffen the headrest when a collision is detected. The dilatant fluid responds essentially instantaneously, and before the passenger's head strikes the headrest. In this way, the headrest supplies comfortable soft cushioned head support during normal driving but stiffens to provide the needed stronger support in the event of impact.

Figures 11, 12:
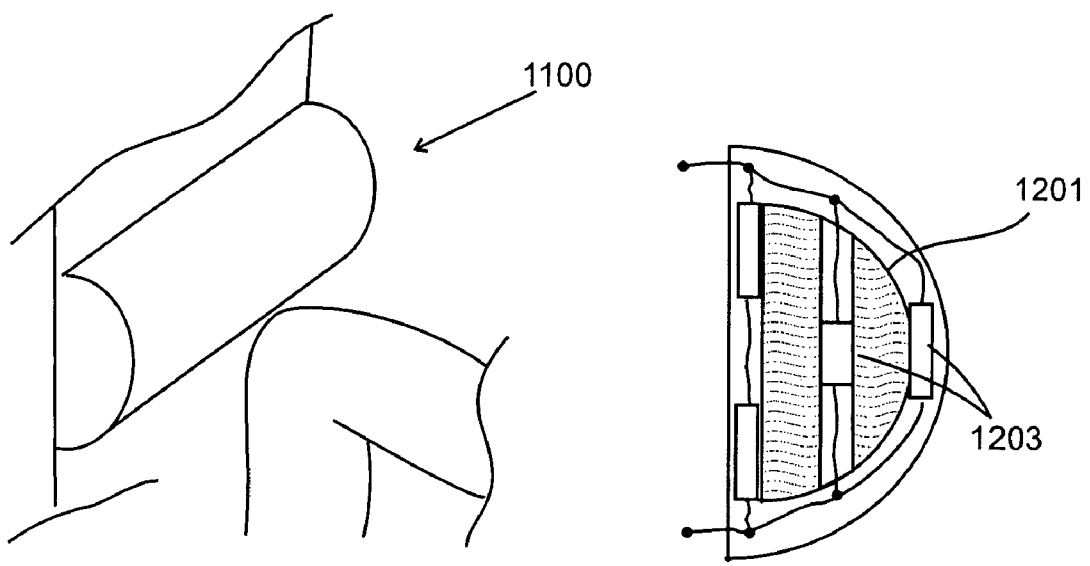
FIGS. 11 and 12 depict a knee bolster having controllable stiffness.

FIGS. 11 and 12 illustrate a knee bolster fitted to an automobile or bus seat back or an airplane bulkhead which provides a soft cushion under normal conditions but which stiffens in the event of impact. The bolster seen at 1100 in FIG. 11 is shown in cross-section in FIG. 12 and employs a dilatant fluid at 1201 sandwiched between layers which include piezoelectric oscillating plates, two of which are seen at 1203.

In addition to the illustrative applications described above, the principles of the invention may be applied to advantage in many other applications where adaptive stiffness or energy-absorbing materials are used, including robotics, haptic devices utilizing force-feedback, and medical devices like catheters, surgical gloves etc.

In the illustrative embodiments described above, piezoelectric devices were used to subject a shear-thickening fluid to controlled oscillations to vary its stiffness. A number of different kinds of transducers can be used to externally activate shear-thickening fluids. The associated electronics that is connected to these transducers will usually comprise of, but is not limited to, a D.C. or A.C. power supply such as a battery, automotive battery etc. and a function generator or a frequency controller to convert the power from the source into an applied oscillating current or voltage of the desired amplitude and frequency. Some transducers may also require additional electronic components, such as a voltage amplifier in case of piezoelectric actuators. Generally speaking, the amplitude of the oscillations can be controlled using a voltage controlled power supply while the frequency can be controlled using a function generator, frequency controller or variable frequency oscillator.

Figure 13:
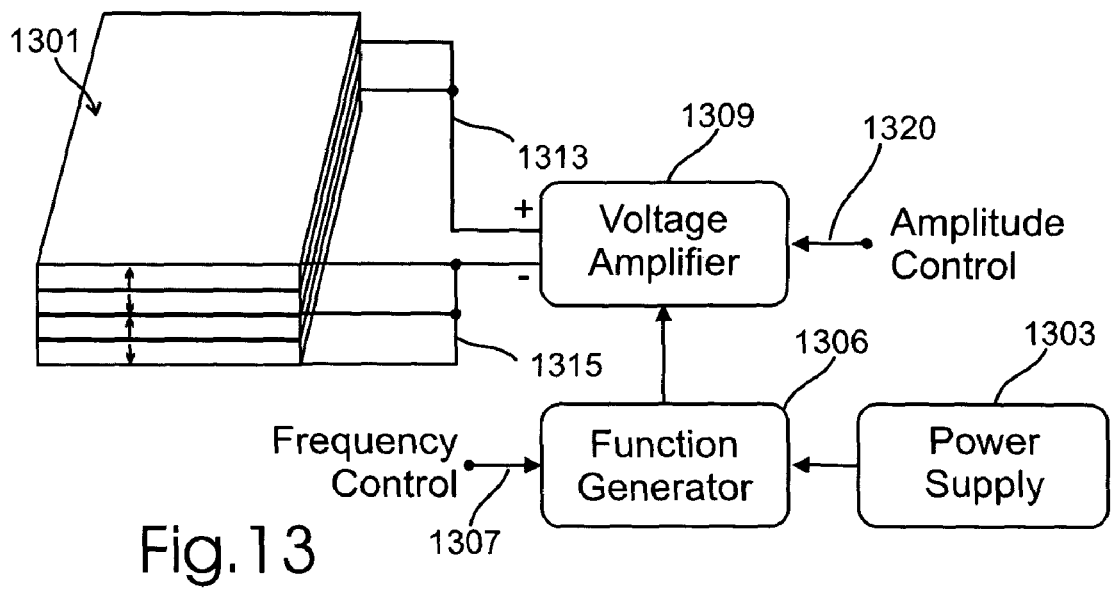
FIG. 13 is a schematic block diagram illustrating the control electronics used in conjunction with a piezoelectric device stack actuator.

FIG. 13 illustrates the use of a stacked piezoelectric actuator seen at 1301. Electrical power from an available source 1303 is applied to a function generator 1306 which produces a waveform having a frequency which can be varied by applying a variable control voltage (for example, using a potentiometer) at 1307. The resulting variable frequency waveform is applied to a gain controlled amplifier 1309 which applies a variable frequency, variable amplitude voltage waveform across the supply conductors 1313 and 1315. A variable control voltage applied to gain control input terminal 1320 of the amplifier 1309 controls the amplitude of the voltage applied across the supply conductors 1313 and 1315. The stacked piezoelectric actuator consists of four stacked piezoelectric plates separated by conductive layers. The outermost conductive layers and a center layer are connected to the supply conductor 1315 while the two interior layers which are positioned between the center and outer layers are connected to the supply terminal 1313. Thus, the voltage applied to the actuator stack by the amplifier 1309 causes the actuator to apply variable frequency, variable amplitude oscillations to a dilatant fluid (not shown in FIG. 13) which is acoustically coupled to the actuator, thereby controlling the stiffness of the dilatant fluid.

Figure 14:
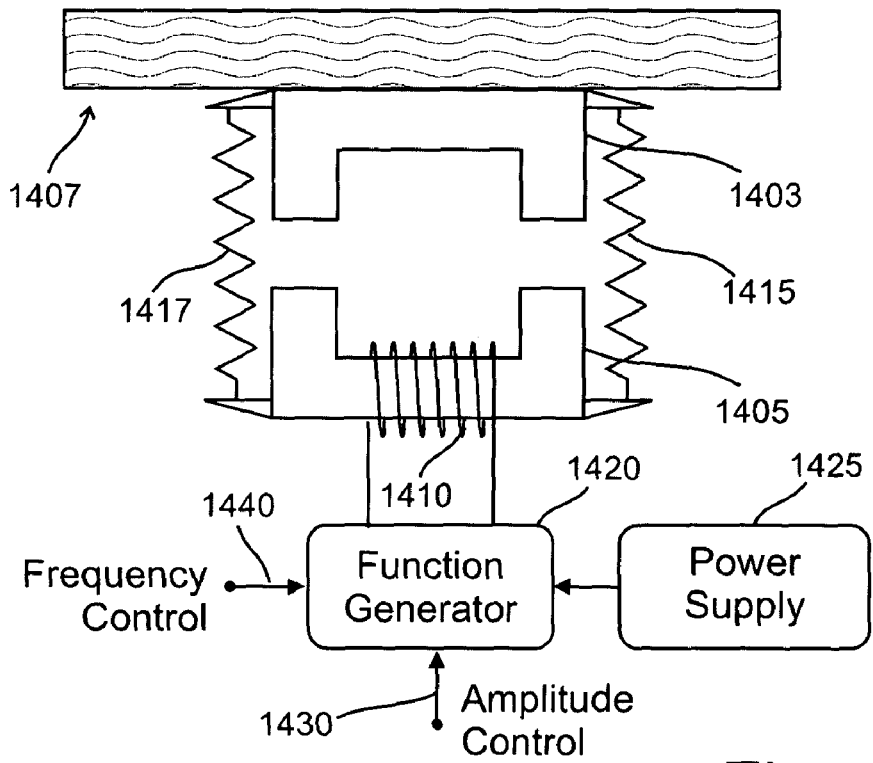
FIG. 14 is a schematic block diagram illustrating a voice coil type actuator and associated drive electronics.

FIG. 14 illustrates an alternative electromagnetic actuator, such as a voice coil, that can be used to apply controlled vibratory oscillation to a shear-responsive fluid. The electromagnetic actuator consists of a pair of ferromagnetic pole pieces 1403 and 1405 and a drive coil 1407 wound on the pole piece 1405. The pole piece 1403 is in acoustic contact with a dilatant fluid indicated generally at 1410. Springs illustrated at 1415 and 1417 resiliently support the two pole pieces in spaced relation from one another such that, when an oscillating current is passed through the drive coil 1407 to apply a vibratory magnetizing force between the two pole pieces, vibratory energy is applied to the dilatant fluid 1410. The drive coil 1407 is driven by a variable amplitude, variable frequency current from a function generator 1420 powered from a power supply 1425. The function generator 1420 has a amplitude control input 1430 for accepting a control voltage that varies the intensity of the current delivered to the drive coil 1407, and further has a frequency control input 1440 for accepting a second control voltage that varies the frequency of the current waveform applied to the coil 1407.

Figure 15:
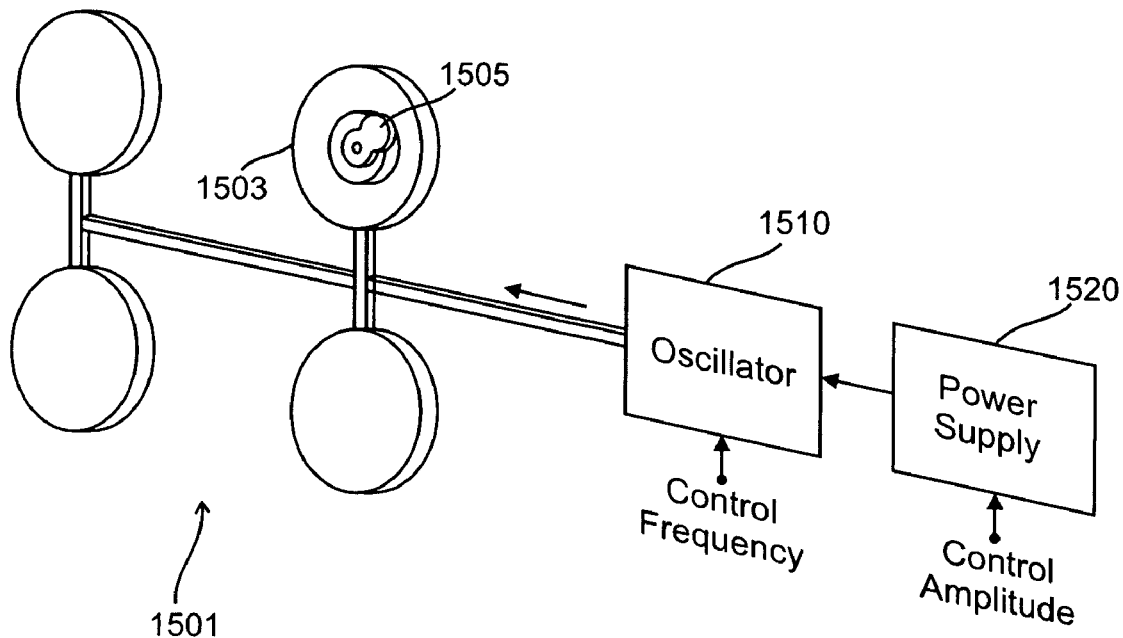
FIG. 15 illustrates an array of motor driven swinging arm actuators.

FIG. 15 shows another form of actuator for applying variable frequency oscillations to a shear responsive fluid. The actuator consists of an array of swinging armature actuators shown generally at 1501. Each individual actuator consists of a small electric motor 1503 whose armature drives an eccentric swinging arm 1505. The motor armature rotates synchronously with the frequency of a drive signal from an oscillator 1510 powered from a power supply 1520. A control signal applied to the oscillator 1510 varies the frequency of the drive signal applied to the synchronous motor 1503, varying the motor speed and hence varying the frequency of vibrations applied to the shear responsive fluid (not shown in FIG. 15) that is in vibratory contact with the array of swinging arm actuators 1501.

Embodiments of the invention may work in one of two different modes of operation: impact mode and continuous use. In the impact mode, the device responds to imposed stress and therefore imposed strain rate which activate the dilatant fluid. In the impact mode, the fluid remains at a low viscosity state before impact and is "primed" with by applying a small imposed oscillatory field to the fluid so that it responds to even small deformation impacts whereas, with no oscillation applied, the device responds to larger impacts by undergoing a transition to high viscosity and high damping state upon impact. Thus, a given device designed to respond properly to large impacts can provide improved response to small impacts by applying a small controlled high frequency oscillation to the fluid to partially stiffen the device for small impacts.

Figure 16:
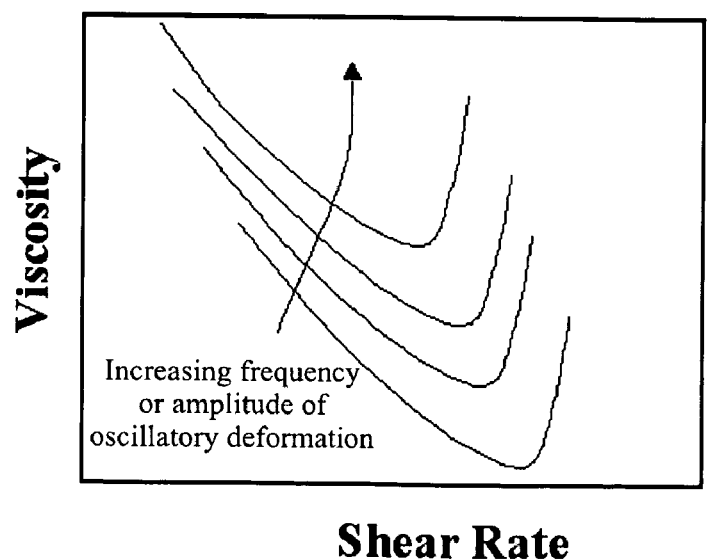
FIG. 16 is a chart showing the manner in which the viscosity of a shear responsive fluid is controlled by applied oscillations of varying frequency.

In the continuous use mode, an oscillatory field is applied to change the material properties of the system. Specifically, the device's operating point on the viscosity curve can be shifted by adjusting the frequency and amplitude of the oscillations as shown in FIG. 16 which shows how the viscosity curve may shifted upward by increasing the frequency of the applied control oscillations, and thereby stiffen the devices response to impacts which subject the device to a given shear rate. In this way, the applied control oscillations can be varied in frequency and/or amplitude to tailor the material properties to satisfy the requirements of specific applications. In the case of applied control vibrations the system response can be shifted (by frequency ranging from $10^{-3}$-$10^5$ Hz and strain ranging from $10^{-2}$-100), to be able to absorb impact energies within a range of timescales by effectively controlling the critical deformation rate. By way of example, for a 60% volume fraction silica suspension in ethylene glycol, a desired shear thickening can be achieved at frequency that ranges between $10^{-1}$-$10^2$ rad/sec with strains that range between 1-50.

The devices used to apply vibratory energy to the shear responsive fluid, here called "actuators" or "transducers," convert one form of energy to another. The present invention may employ actuators that convert any form of input energy into oscillatory motion with controllable frequency and amplitude. A number of such transducers are available commercially and have been described in issued patents. The type of transducer that is used will depend on the needs of the particular application including specific power levels, geometrical constraints, desired output oscillation frequency and amplitude. The manner in which typical transducers are driven using control electronics has been illustrated above. Actuators than may be used as components in appropriate applications include the following which are described in the identified issued patents, the disclosures of which are incorporated herein by reference:

(a) Piezoelectric actuators available from PI (Physik Instrumente) L. P. of Auburn, Mass., including sheet/stack devices PI (P-007, P-056) described in U.S. Pat. No. 5,834,879 and bimorph devices PI (P-288, P-289) described in U.S. Pat. No. 4,625,137. See also, U.S. Pat. Nos. 4,812,698 and 6,741,710;

(b) Electromagnetic actuators, including swinging armature and magnetic motor devices available from Jinlong Machinery & Electronics Co., Ltd. of Zhejiang, China (model nos. 4AL- and 4KL-) and from SANYO E&E America Company of Bensenville, Ill. (model nols. 4L-M- and 5L-M-); voice coil actuators available from Koyo Electronics (AK Series) and from Dain Electronics (model M36A550) and described in U.S. Pat. No. 6,553,126;

(c) Fluidic devices, including the pneumatic motors available from All Air Inc. (MMF models) and described in U.S. Pat. No. 6,807,892;

(d) Shaped memory alloy devices available from the Memory Alloy Division of G. RAU GmbH (see U.S. Pat. Nos. 4,700,541 and 5,061,914;

(e) Magnetorestrictive devices, including the AU-1 models available from Etrema Products (see U.S. Pat. No. 5,850, 109; and (f) Electroactive polymers, including the Micromuscle available from Hitech Polymers (see U.S. Pat. No. 6,781,284.

Suitable shear thickening fluids may be formed by mixing the compounds listed in the table below with solvents such as such as alcohols and water (30%-65% particles v/v):

| Compound | Batch/Particle Name | Size | Vendor |
| --- | --- | --- | --- |
| Silica | SP-03/SP-1B | 300 nm/1 µm | Fuso Chemicals |
| Silica | MP4540 | 460 nm | Nissan Chemicals |
| Fumed Silica | D150 | 14 nm | Degussa Corporation |
| Corn Starch | S78931-1 | 100-800 nm | Fisher Scientific |

Conclusion

It is to be understood that the methods and apparatus which have been described above are merely illustrative applications of the principles of the invention. Numerous modifications may be made by those skilled in the art without departing from the true spirit and scope of the invention.

What is claimed is:

1. A method for controlling the rheological properties of a dilatant material to control its response to stress applied to said material by a load or impact comprising the step of applying a controlled, oscillatory deformation stress to said dilatant material from an external source separate from said load or impact at a controlled deformation rate to control the viscosity of said material.

2. A method for controlling the rheological properties of a dilatant material as set forth in claim 1 wherein said step of applying a controlled, oscillatory deformation stress to said dilatant material comprises varying the magnitude of said oscillatory deformation stress to vary said controlled deformation rate.

3. A method for controlling the rheological properties of a dilatant material as set forth in claim 1 wherein said step of applying a controlled, oscillatory deformation stress to said dilatant material comprises varying the frequency of said oscillatory deformation stress to vary said controlled deformation rate.

4. A method for controlling the rheological properties of a dilatant material as set forth in claim 1 wherein said step of applying a controlled, oscillatory deformation stress to said dilatant material comprises varying the magnitude and frequency of said oscillatory deformation stress to vary said controlled deformation rate.

5. A method for controlling the rheological properties of a dilatant material as set forth in claim 1 wherein said step of applying a controlled, oscillatory deformation stress to said dilatant material comprises controlling the magnitude of said controlled deformation rate within a range extending from a minimum applied deformation rate at which said dilatant material exhibits a reduced viscosity and a maximum applied deformation rate at which said dilatant material exhibits an elevated viscosity.

6. A method for controlling the rheological properties of a dilatant material as set forth in claim 1 wherein said step of applying a controlled, oscillatory deformation stress to said dilatant material comprises controlling the magnitude of said controlled deformation rate within a range of deformation rate magnitudes within which the viscosity of said dilatant material varies as said controlled deformation rate varies.

7. A method for controlling the rheological properties of a dilatant material as set forth in claim 1 wherein said step of applying a controlled, oscillatory deformation stress to said dilatant material comprises controlling the magnitude of said controlled deformation rate within a range in which said dilatant material thickens as said deformation rate increases.

8. An active energy management structure comprising, in combination,
a dilatant material for absorbing or redistributing impact energy applied to said dilatant material from an external impact energy source,
a transducer for applying a controlled vibratory stress or strain to said dilatant material separate from the stress or strain applied to said dilatant material from said impact energy source to cause the viscosity of said dilatant material to increase as the rate of deformation of said dilatant material induced by said vibratory stress or strain increases.

9. An active energy management structure as set forth in claim 8 further including means coupled to said transducer and responsive to the actual or anticipated magnitude of said impact energy for varying said controlled vibratory stress or strain to increase said viscosity as said magnitude increases.

10. An active energy management structure as set forth in claim 8 wherein said transducer is mechanically coupled to said dilatant material.

11. An active energy management structure as set forth in claim 8 wherein said dilatant material is positioned within a container having one or more side walls and wherein said transducer is attached to said one or more side walls.

12. An active energy management structure as set forth in claim 8 wherein the magnitude of said controlled vibratory stress or strain is varied to adjust said rate of deformation.

13. An active energy management structure as set forth in claim 8 wherein the frequency of said controlled vibratory stress or strain is varied to adjust said rate of deformation.

14. An active energy management structure as set forth in claim 8 wherein the magnitude and the frequency of said controlled vibratory stress or strain are varied to adjust said rate of deformation.

* * * * *